United States Patent [19]

Leanza et al.

[11] Patent Number: 4,713,451
[45] Date of Patent: Dec. 15, 1987

[54] CRYSTALLINE DIMETHYLIMINOTHIENAMYCIN

[75] Inventors: William J. Leanza, Berkeley Heights; Kenneth J. Wildonger, Bridgewater, both of N.J.

[73] Assignee: Merck & Co., Inc., Rahway, N.J.

[21] Appl. No.: 597,944

[22] Filed: Apr. 9, 1984

[51] Int. Cl.$^4$ .................... C07D 487/04; A61K 31/40
[52] U.S. Cl. .................... 540/350; 514/210; 540/310
[58] Field of Search .............. 260/245.2 T, 245.2 R; 424/270; 540/350; 514/310

[56] References Cited

U.S. PATENT DOCUMENTS 4,260,543  4/1981  Miller .................... 540/350

FOREIGN PATENT DOCUMENTS 0050334  4/1982  European Pat. Off. .

OTHER PUBLICATIONS

*The Merck Index* (Merck), 10th Ed., Merck and Co., Inc., Rahway, N.J., (1983), pp. 9149–9150.
*Burger's Medicinal Chemistry* (Burger's), 4th Ed., Part 11, John Wiley and Sons, New York, (1979), pp. 153–155.

*Primary Examiner*—Nicholas S. Rizzo
*Attorney, Agent, or Firm*—Hesna J. Pfeiffer; Raymond M. Speer

[57] ABSTRACT

Crystalline dimethyliminothienamycin having the formula

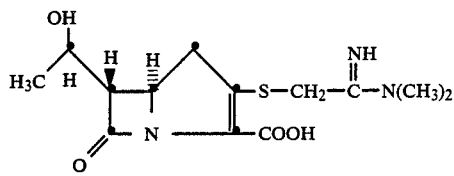

and its preparation are disclosed.

1 Claim, No Drawings

CRYSTALLINE DIMETHYLIMINOTHIENAMYCIN

BACKGROUND OF THE INVENTION

The invention concerns crystalline 5R,6S-6-(1-R-hydroxyethyl)-2-(N,N-dimethylamidinomethylthio)-carbapen-2-em-3-carboxylic acid, also referred to herein as dimethyliminothienamycin.

Dimethyliminothienamycin has the formula

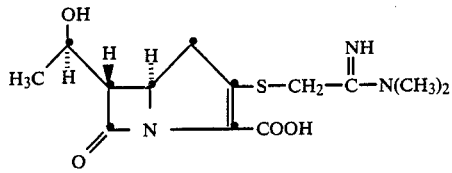

It is a broad spectrum antibiotic of the carbapenem class. Its preparation (and use) in non-crystalline form is described in EUROPEAN PATENT APPLICATION No. 81-108 420,1.

A crystalline form of I has been prepared. Crystalline I is more stable than the non-crystalline form while retaining the antibiotic activity.

SUMMARY OF THE INVENTION

Crystalline form of dimethyliminothienamycin having the formula

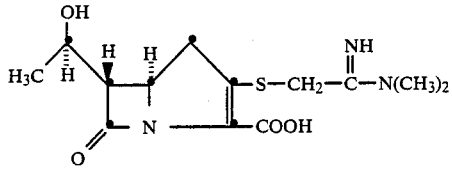

DETAILED DESCRIPTION OF THE INVENTION

An embodiment of the invention is a crystalline form of dimethyliminothienamycin having the formula

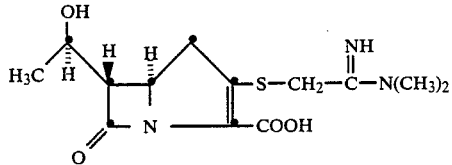

Preparation of the non-crystalline formula I compound is disclosed in EUROPEAN PATENT APPLICATION No. 81-108-420.1. Its use as an antibiotic at dosages and in modes of administration is also disclosed in said European Patent Application.

A crystalline form of I has been prepared. This crystalline form has the same utility as the non-crystalline moiety. The crystalline form is improved in that it is more stable, i.e. it has greater shelf life, than the non-crystalline form.

The crystalline form of I is prepared as described in the following example.

EXAMPLE 1

A lyophilized sample of 5R,6S-6-(1-R-hydroxyethyl, 2-(N,N-dimethylamidinomethylthio)carbapen-2-em-3-carboxylic acid (150 mg) is dissolved in methanol (3 ml) and seeded with crystals obtained by a procedure described immediately below. The solution is stirred in an ice-bath. After 2 hours the crystals are recoverd by filtration, washed with 1 ml of methanol and dried at room temperature under vacuum to yield 90 mg of crystalline dimethylimino thienamycin.

The seed crystals employed in the above crystallization are prepared by the following procedure. A lyophilized sample of dimethyliminothienamycin (8 mg) is dissolved in methanol (0.05 ml), diluted with ethyl acetate until cloudiness results, and stored at room temperature. After two days, small clumps of crystals are observed on the walls of the tube. U.V.λmax 294 nmε8,360.

Anal: ($C_{13}H_{19}N_3S_4$) Calc'd C, 49.83; H, 6.11; N, 13.41. Found: C, 49.54; H, 6.45; N, 13.07.

The x-ray powder diffraction patterns were obtained for two samples of crystalline dimethylimino thienamycin prepared as in Example 1. The angles ($2\theta$) and intensities of the 19 major and minor peaks were measured, and the d-spacings and relative intensities were determined. These values were then averaged for the two samples. The d-spacing values were in almost complete accord between the samples. Relative intensities agreed to within 10% absolute.

Table I contains the calculated d-spacings and relative intensities averaged for the two samples.

TABLE I

| Average d-Spacings and Relative Intensities | |
|---|---|
| d-Spacing | Relative Intensity |
| 8.15 | 8.29 |
| 7.62 | 7.02 |
| 6.51 | 17.73 |
| 5.27 | 16.40 |
| 4.85 | 100.00 |
| 4.76 | 35.05 |
| 4.45 | 32.98 |
| 4.14 | 24.01 |
| 3.90 | 30.40 |
| 3.85 | 18.71 |
| 3.79 | 9.90 |
| 3.66 | 8.46 |
| 3.25 | 30.80 |
| 3.16 | 15.20 |
| 3.07 | 18.02 |
| 3.02 | 26.72 |
| 2.90 | 12.95 |
| 2.71 | 7.83 |
| 2.62 | 11.34 |

Crystalline dimethylimino thienamycin has a solubility in water of ca 350 mg/ml. In an accelerated solid state stability test, 92% remained after 2 weeks at 60° C. compared with 58% remaining of the lyophilized non-crystalline form, under the same conditions.

Claims to the invention follow.

What is claimed is:

1. Crystalline 5R,6S-6-(1-R-hydroxyethyl) 2-(N,N-dimethylamidinomethylthio)-carbapen 2-em-3-carboxylic acid, having the formula;

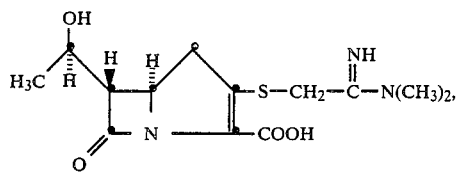
and having the following X-ray powder diffraction parameters:
| d-Spacing | Relative Intensity |
|---|---|
| 8.15 | 8.29 |
| 7.62 | 7.02 |
| 6.51 | 17.73 |
| 5.27 | 16.40 |
| 4.85 | 100.00 |
| 4.76 | 35.05 |
| 4.45 | 32.98 |
| 4.14 | 24.01 |
| 3.90 | 30.40 |
| 3.85 | 18.71 |
| 3.79 | 9.90 |
| 3.66 | 8.46 |
| 3.25 | 30.80 |
| 3.16 | 15.20 |
| 3.07 | 18.02 |
| 3.02 | 26.72 |
| 2.90 | 12.95 |
| 2.71 | 7.83 |
| 2.62 | 11.34 |
* * * * *